United States Patent
Pfeiffer

(10) Patent No.: US 6,841,694 B2
(45) Date of Patent: Jan. 11, 2005

(54) PROCESS FOR STABILIZING UNSATURATED ORGANOSILICON COMPOUNDS

(75) Inventor: Juergen Pfeiffer, Burghausen (DE)

(73) Assignee: Wacker-Chemie GmbH, Munich (DE)

( * ) Notice: Subject to any disclaimer, the term of this patent is extended or adjusted under 35 U.S.C. 154(b) by 0 days.

(21) Appl. No.: 10/771,769

(22) Filed: Feb. 4, 2004

(65) Prior Publication Data

US 2004/0171859 A1 Sep. 2, 2004

(30) Foreign Application Priority Data

Feb. 27, 2003 (DE) .......................................... 103 08 579

(51) Int. Cl.⁷ .................................................. C07F 7/02
(52) U.S. Cl. ..................................... 556/401; 556/438
(58) Field of Search ................................. 556/401, 438

(56) References Cited

U.S. PATENT DOCUMENTS

| 5,145,979 A | 9/1992 | Takatsuma et al. |
| 5,235,051 A | 8/1993 | Bernhardt et al. |
| 6,608,225 B1 | 8/2003 | Larson et al. |
| 2002/0151736 A1 | 10/2002 | Pfeiffer et al. |

FOREIGN PATENT DOCUMENTS

| DE | 44 37 667 A1 | 4/1996 |
| EP | 0 483 479 A1 | 5/1992 |
| EP | 0 483 480 | 5/1992 |
| EP | 0 708 081 | 6/1999 |
| EP | 1 004 587 A2 | 5/2000 |
| EP | 1 249 454 | 10/2002 |
| WO | WO 00/75148 A | 12/2000 |

OTHER PUBLICATIONS

English Derwent Abstract AN 1996–201982[2] corresp. to DE 44 37 667 A1.
English Derwent Abstract AN 1992–15229[19] corresp. to EP 0 483 480 A.
English Derwent Abstract AN 1996–201982[21] corresp. to EP 0 708 081 B1.

*Primary Examiner*—Samuel Barts
(74) *Attorney, Agent, or Firm*—Brooks Kushman P.C.

(57) ABSTRACT

A process for stabilizing organosilicon compounds bearing unsaturated groups during their preparation, distillation, and/or storage, the organosilicon compounds bearing unsaturated groups having been obtained by reacting a haloalkylsilane with a salt of an unsaturated organic acid, by adding one or more compounds of the formula I

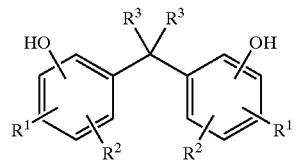

(I)

wherein $R^1$ and $R^2$ are identical or different linear or branched $C_{1-20}$ alkyl, and the radicals $R^3$ are identical or different and are hydrogen or linear or branched alkyl radicals having 1–20 carbon atoms.

8 Claims, No Drawings

PROCESS FOR STABILIZING UNSATURATED ORGANOSILICON COMPOUNDS

BACKGROUND OF THE INVENTION

1. Field of the Invention

The invention relates to a process for stabilizing unsaturated organosilicon compounds.

2. Background Art

Organosilicon compounds having unsaturated organic functional groups such as vinyl, acryloyl or methacryloyl groups are widely used as adhesion promoters between inorganic and organic materials, for example in sizes for glass fibers, as crosslinking agents in organic polymers, and as agents for the treatment of fillers.

Preparation processes for such compounds include, for example, the reaction between silanes having SiH bonds and unsaturated (optionally polyunsaturated) organic compounds, generally referred to as "hydrosilylation", which is catalyzed by metal compounds, and the reaction of haloalkyl-substituted alkoxysilanes with salts of acrylic or methacrylic acid, referred to as "nucleophilic substitution". Common to all these processes is that they take place exothermically at elevated temperatures, giving rise to the risk of polymerization of the products during the reaction by reaction of the unsaturated organic group, with the result that product is lost and reaction apparatuses used have to be cleaned by complicated procedures. Moreover, the silanes bearing unsaturated organic groups are generally purified by distillation, the thermal energy required for this purpose also giving rise to a considerable risk of polymerization. Finally, there is also the risk of polymerization during storage of these compounds.

Numerous processes for preventing the polymerization of organosilicon compounds carrying unsaturated organic groups include the use of so called free radical polymerization inhibitors. These compounds are used during the preparation, regardless of the preparation route, during the work up by distillation, and during storage of the organosilicon compounds bearing unsaturated groups.

U.S. Pat. No. 5,145,979 describes a mixture of a sterically hindered phenol, an aromatic amine and/or an alkylamine as having a stabilizing effect in the preparation of organosilicon compounds having unsaturated organic groups by hydrosilylation. DE 4 437 667 A1, EP 0 483 479 A1 and EP 0 483 480 A1 describe the use of N,N'-diphenyl-p-phenylenediamine ("DPPA") for stabilization during the preparation of unsaturated organosilicon compounds by nucleophilic substitution.

EP 1 004 587 A2 discloses use of a combination of two different polymerization inhibitors: a compound from the class consisting of N,N'-disubstituted p-phenylenediamines, and a compound from the class consisting of the 2,6-di-tert-butyl-4-alkylphenols.

EP 708 081 B1, on the other hand, describes the use of N,N'-disubstituted p-quinodiimines, alone or in combination with other compounds having a stabilizing effect, in the preparation of organosilicon compounds bearing unsaturated groups by nucleophilic substitution.

Common to all processes in which a plurality of inhibitors is used is that one of the polymerization inhibitors employed has a very high boiling point and thus stabilizes the bottom product, while another has a volatility similar to that of the product to be distilled and thus stabilizes the gas phase. However, the use of amines such as N,N'-diphenyl-p-phenylenediamine, or sterically hindered phenols containing amino groups such as 2,6-dialkyl4-N,N-dialkyl-aminomethylphenols, leads to the formation of volatile amine impurities under the thermal conditions of the distillation, which result in the distilled products having a yellow color and an unpleasant odor reminiscent of fish.

Common to the processes described are the further disadvantages that relatively large amounts of stabilizing compound(s) have to be used; that these compounds are often very expensive; and that the processes described often, for example when in contact with an oxygen-containing gas mixture, must be considered safety-critical. In addition, in the case of most of the compounds described, in spite of a stabilizing effect exerted on unsaturated organosilicon compounds, there is still a residual risk that the unsaturated organosilicon compounds will be polymerized and hence lost.

SUMMARY OF THE INVENTION

It was therefore an object of the present invention to provide compounds which, even in a very small amount, very efficiently prevent the polymerization of unsaturated organosilicon compounds and thus protect resources, without influencing the quality of the product through the formation of colored or odiferous compounds. In particular, this object was to be achieved for the distillation of crude reaction mixtures of organosilicon compounds which have unsaturated groups and were obtained by reacting haloalkyl-silanes with salts of unsaturated organic acids. These and other objects are achieved by the present invention.

Surprisingly, it was found that compounds of the general formula I

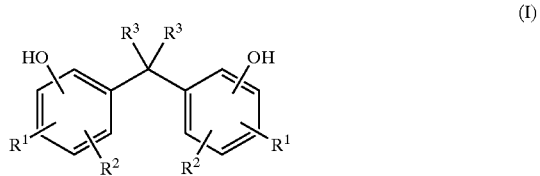

(I)

are outstandingly suitable for stabilizing unsaturated, silicon-containing compounds during their preparation and/or distillation and/or storage, the organosilicon compounds bearing unsaturated groups being obtained by the reaction of haloalkylsilanes with salts of unsaturated acids. In the absence of further stabilizers, highly pure, colorless products which are odorless apart from their natural odor may be obtained.

DETAILED DESCRIPTION OF THE PREFERRED EMBODIMENT(S)

The invention thus relates to a process for stabilizing organosilicon compounds bearing unsaturated groups, preferably corresponding to compounds of the formula II:

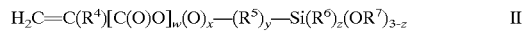

II during their preparation and/or distillation and/or storage, $R^4$ being a hydrogen atom or a linear or branched hydrocarbon radical having 1–10 carbon atoms, $R^5$ being a linear, cyclic or branched hydrocarbon radical having 1–40 carbon atoms which optionally may contain one or more hetero atoms selected from the elements nitrogen, oxygen, sulfur and phosphorus, $R^6$ and $R^7$ being linear, cyclic or branched hydrocarbon radicals having 1–10 carbon atoms, wherein w may assume the values 0 or 1, x the values 0 or 1, y the values 0 or 1, and z the values 0, 1 or 2, it not being permitted for w and x both to be 1 simultaneously, the compounds of the formula II having been obtained by reacting a haloalkylsilane with a salt of an unsaturated organic acid, with a stabilizer comprising at least one compound of the general formula I

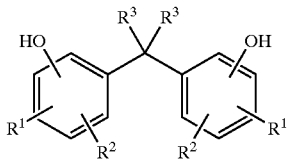
(I)

$R^1$ and $R^2$ being identical or different linear or branched alkyl chains having 1–20 carbon atoms and the radicals $R^3$ being identical or different substituents selected from the groups consisting of hydrogen or linear or branched alkyl radicals having 1–20 carbon atoms.

$R^1$ and $R^2$ in formula I are identical or different linear or branched alkyl chains having 1–20 carbon atoms which may optionally contain hetero atoms such as oxygen, sulfur, phosphorus or nitrogen. Branched alkyl radicals, such as the isopropyl, isobutyl or tert-butyl radical are preferred, the tert-butyl radical being particularly preferred. In the compounds of the formula I, the radicals $R^1$ and $R^2$ and the hydroxyl group may assume any desired positions on the aromatic nucleus; the hydroxyl group and the methylene bridge are preferably in the ortho or para position relative to one another and the radicals $R^1$ and $R^2$ are preferably in the meta or para position relative to one another.

The radicals $R^3$ are identical or different substituents selected from the groups consisting of hydrogen or linear or branched alkyl radicals having 1–20 carbon atoms, which may be saturated or unsaturated and/or substituted by hetero atoms. The radicals $R^3$ are preferably hydrogen or linear or branched hydrocarbon radicals having 1–4 carbon atoms, most preferably hydrogen.

Examples of the compounds of the formula I include 4,4'-methylenebis(2,6-di-tert-butylphenol), 2,2'-methylenebis(3,5-di-tert-butylphenol), 4,4-methylenebis(2,6-diisopropylphenol) and 2,2'-methylenebis(3,5-diisopropylphenol). The use of 4,4'-methylenebis(2,6di-tert-butylphenol, obtainable under the trade names Ionox 220 (Degussa AG) and Ralox 02 S (Raschig GmbH), is particularly preferred.

The compounds according to the invention are particularly suitable for stabilizing unsaturated organosilicon compounds of the formula

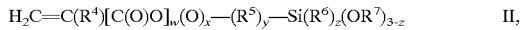

$R^4$ being a hydrogen atom or a linear or branched hydrocarbon radical having 1–10 carbon atoms, $R^5$ being a linear, cyclic or branched hydrocarbon radical having 1–40 carbon atoms which may optionally contain one or more hetero atoms selected from the elements nitrogen, oxygen, sulfur and phosphorus, $R^6$ and $R^7$ being linear, cyclic or branched hydrocarbon radicals having 1–10 carbon atoms, and w assuming the values 0 or 1, x the values 0 or 1, y the values 0 or 1, and z the values 0, 1 or 2, it not being permitted for w and x both to be 1 simultaneously.

Examples of organosilicon compounds of the formula II which have unsaturated groups and which can be stabilized with the compounds of the formula I according to the invention are acryloylsilanes, such as, for example, acryloyloxymethyltrimethoxysilane, acryloyloxymethyltriethoxysilane, acryloyloxymethyltriphenoxysilane, acryloyloxymethyltriisopropoxysilane, acryloyloxymethyltris(2-methoxyethoxy)silane, acryloyloxymethyl(methyl)dimethoxysilane, acryloyloxymethyl(methyl)diethoxysilane, acryloyloxymethyl(methyl)diphenoxysilane, acryloyloxymethyl(methyl)diisopropoxysilane, acryloyloxymethyl(methyl)bis(2-methoxyethoxy)silane, acryloyloxymethyl(dimethyl)methoxysilane, acryloyloxymethyl(dimethyl)ethoxysilane, acryloyloxymethyl(dimethyl)phenoxysilane, acryloyloxymethyl(dimethyl)isopropoxysilane, acryloyloxymethyl(dimethyl)(2-methoxyethoxy)silane, 3acryloyloxypropyltrimethoxysilane, 3-acryloyloxypropyltriethoxysilane, 3-acryloyloxypropyltriphenoxysilane, 3-acryloyloxypropyltriisopropoxysilane, 3-acryloyloxypropyltris(2-methoxyethoxy)silane, 3-acryloyloxypropyl(methyl)dirnethoxysilane, 3-acryloyloxypropyl(methyl)diethoxysilane, 3-acryloyloxypropyl(methyl)diphenoxysilane, 3-acryloyloxypropyl(methyl)diisopropoxysilane, 3-acryloyloxypropyl(methyl)bis(2-methoxyethoxyl)silane, 3-acryloyloxypropyl(dimethyl)methoxysilane, 3-acryloyloxypropyl(dimethyl)ethoxysilane, 3-acryloyloxypropyl(dimethyl)phenoxysilane, 3-acryloyloxypropyl(dimethyl)isopropoxysilane or 3-acryloyloxypropyl(dimethyl)(2-methoxyethoxy)silane, or methacryloylsilanes, such as, for example, methacryloyloxymethyltrimethoxysilane, methacryloyloxymethyltriethoxysilane, methacryloyloxymethyltriphenoxysilane, methacryloyloxymethyltriisopropoxysilane, methacryloyloxymethyltris(2-methoxyethoxy)silane, methacryloyloxymethyl(methyl)dimethoxysilane, methacryloyloxy(methyl)diethoxysilane, methacryloyloxymethyl(methyl)diphenoxysilane, methacryloyloxymethyl(methyl)diisopropoxysilane, methacryloyloxymethyl(methyl)bis(2-methoxyethoxy)silane, methacryloyloxymethyl(dimethyl)methoxysilane, methacryloyloxymethyl(dimethyl)ethoxysilane, methacryloyloxymethyl(dimethyl)phenoxysilane, methacryloyloxymethyl(dimethyl)isopropoxysilane, methacryloyloxymethyl(dimethyl)(2-methoxyethoxy)silane, 3-methacryloyloxypropyltrimethoxysilane, 3-methacryloyloxypropyltriethoxysilane, 3-methacryloyloxypropyltriphenoxysilane, 3-methacryloyloxypropyltriisopropoxysilane, 3-methacryloyloxypropyltris(2-methoxyethoxy)silane, 3-methacryloyloxypropyl(methyl)dimethoxysilane, 3-methacryloyloxypropyl(methyl)diethoxysilane, 3-methacryloyloxypropyl(methyl)diphenoxysilane, 3-methacryloyloxypropyl(methyl)diisopropoxysilane, 3-methacryloyloxypropyl(methyl)bis(2-methoxyethoxy)silane, 3-methacryloyloxypropyl(dimethyl)methoxysilane, 3-methacryloyloxypropyl(dimethyl)ethoxysilane, 3-methacryloyloxypropyl(dimethyl)phenoxysilane, 3-methacryloyloxypropyl(dimethyl)isopropoxysilane and 3-methacryloyloxypropyl(dimethyl)(2-methoxyethoxy)silane.

The compounds of the formula I which can be used according to the invention can be employed for stabilizing unsaturated organosilicon compounds of the formula II during the preparation thereof, during purification by distillation, or for stabilization during prolonged storage, e.g. even months or years.

The distillative purification of a crude mixture of organosilicon compounds of the formula II bearing unsaturated groups employing inhibitors of the general formula I can be carried out by generally known methods, for example by batch distillation from a stirrer with or without a rectification column, by short-path distillation, for example using a thin-film or falling-film evaporator, or by any other distillative procedures known to the art.

The compounds of the formula I which are used as stabilizers can be employed in any desired amount provided that this amount is effective for substantially preventing the polymerization of unsaturated organosilicon compound of the formula II. Preferably, the compounds of the formula I are used in an amount of from 0.001 to 1 percent by weight, most preferably in an amount of 0.005 to 0.5 percent by weight, based on the weight of organic silicon compound bearing unsaturated groups.

The compounds of the formula I can be used either alone or in combination with one or more further stabilizers in any desired amount. Examples of such further stabilizers are aromatic or aliphatic amines such as N,N-diphenyl-p-phenylenediamine, other sterically hindered phenols, such as 2,6-di-tert-butyl-4-methylphenol, aromatic ethers or quinones such as hydroquinone monomethyl ether, or organic radicals such as 2,2,6,6-tetramethylpiperidinyl oxide ("TEMPO").

These compounds are preferably used in the same amounts as the compounds of the formula I. The use of one or more compounds of the formula I alone is particularly preferred.

The preparation of the unsaturated organosilicon compounds of the formula II which bear unsaturated groups, when using the stabilizing compounds of the formula I, is carried out by reacting a haloalkylsilicon compound with a salt of an unsaturated organic acid, optionally in the presence of a phase-transfer catalyst. The preparation may be carried out at a temperature of 80–160° C., preferably at 90–150° C. and more preferably at 100–120° C. The preparation can take place at any desired pressure, preferably at 0.1–3 bar and most preferably, at 250–1013 mbar.

EXAMPLE 1

A crude reaction mixture containing of 5% of acetone, 94% of 3-methacryloyloxypropyltrimethoxysilane and 1% of the corresponding disiloxane was obtained by heating potassium methacrylate with 3-chloropropyltrimethoxysilane (molar ratio 1.05:1) in the presence of 1% of nBu$_4$PCl, 5% of acetone and 500 ppm of 4,4'-methylenebis(2,6-di-tert-butylphenol) to 115° C. for 4 hours and effecting filtration.

After removal of the acetone under reduced pressure, distillation via a distillation head at a still pressure of 3 mbar (boiling point 103° C.) led to 3-methacryloyloxypropyltrimnethoxysilane having a purity of 99.6%. The product had an APHA color number of 3 and had only a slight natural odor. Polymeric material was observed neither in the distillation still nor in the distillation head nor in the receiver. The distillation yield is 95%.

EXAMPLE 2

A crude reaction mixture obtained as in example 1 and comprising 3-methacryloyloxypropyltrimethoxysilane was distilled, after removal of the acetone, over 12 hours at a mixing rate of 100 ml/h by means of a short-path distillation of the Leybold-Heraeus KD 3 type. By setting the temperature and pressure 140° C. and 4 mbar respectively, a discharge of about 5% was established. 3-methacryloyloxypropylsilane having a purity of 99.5%, was odorless, and which exhibited an APHA color number of 6 was obtained. Once again, no polymeric fractions were observed in the distillation apparatus, in the product receiver or in the bottoms.

Comparative Example C3 (Not According to the Invention)

A crude reaction mixture comprising 3-methacryloyloxypropylsilane was obtained as in example 1, except that 1000 ppm of 2,6-di-tert-butyl-4-methylphenol were used instead of 4,4'-methylenebis(2,6-di-tert-butylphenol). After removal of the acetone, 1 kg of this crude product was distilled through a distillation head at 3 mbar (boiling point 103° C.). After 30% of the expected product were obtained, the distillation was stopped since the bottom product of the distillation had gelled. The product obtained had a purity of 99.3%, an APHA color number of 15 and a GC content of 0.11% of 2,6-di-tert-butyl4-methylphenol. This example shows that the high volatility of the polymerization inhibitor not according to the invention leads to a loss of product.

Comparative Example C4 (Not According to the Invention)

A crude reaction mixture comprising 3-methacryloyloxypropylsilane was obtained as in example 1, except that 1000 ppm of 2,6-di-tert-butyl-4-methylphenol and 500 ppm of N,N'-diphenyl-p-phenylenediamine were used instead of 4,4'-methylenebis(2,6-di-tert-butylphenol). After removal of the acetone, 1 kg of this crude product was distilled through a distillation head at 3 mbar (boiling point 103° C.). After 80% of the expected product were obtained, the distillation was stopped since the bottom product of the distillation had gelled. The product obtained had a purity of 99.3%, an APHA color number of 35 and a GC content of 0.09% of 2,6di-tert-butyl4-methylphenol. In addition, the product had an unpleasant, fishy odor. This example shows that, in addition to the volatility of the one polymerization inhibitor, the use of a nonvolatile amine polymerization inhibitor is also disadvantageous, owing to discoloration of the product and an unpleasant odor.

Comparative Example C5 (Not According to the Invention)

A crude reaction mixture comprising 3-methacryloyloxypropylsilane was obtained as in example 1, except that 1 000 ppm of 2,6-di-tert-butyl-4-(N,N-dimethylaminomethyl)phenol were used instead of 4,4'-methylenebis(2,6-di-tert-butylphenol).

After removal of the acetone, 1 kg of this crude product was distilled through a distillation head at 3 mbar (boiling point 103° C.). The product obtained had a purity of 99.5%, an APHA color number of 40 and an unpleasant fishy odor. This example shows that the use of an amine-containing phenolic polymerization inhibitor is disadvantageous owing to discoloration of the product and an unpleasant odor.

The observations during the distillation of further reaction mixtures comprising (meth)acryloyloxyalkylsilanes, which were obtained in each case by reacting corresponding haloalkylsilanes with (meth)acrylic acid salts, are summarized in table 1.

TABLE 1

| No. | Target product | Inhibitor[a] | Dist.[b] | Purity | Odor[c] | APHA |
|---|---|---|---|---|---|---|
| 6 | Methacryloyloxymethyltrimethoxysilane[d] | 500 ppm of Ionox 220 | DH | 99.2 | N | 5 |
| 7 | Methacryloyloxymethyltrimethoxysilane[d] | 500 ppm of Ionox 220 | TFV | 99.1 | N | 8 |
| C8[e] | Methacryloyloxymethyltrimethoxysilane[d] | 1,000 ppm of BHT + 500 ppm of DPPA | DH | 99.4[f] | A | 28 |
| C9[e] | Methacryloyloxymethyltrimethoxysilane[d] | 1,000 ppm of BHT + 500 ppm of DPPA | TFV | 98.7[g] | A | 35 |
| C10[e] | Methacryloyloxymethyltrimethoxysilane[d] | 1,000 ppm of Ethanox 703 | DH | 98.5 | A | 40 |
| C11[e] | Methacryloyloxymethyltrimethoxysilane[d] | 1,000 ppm of Ethanox 703 | TFV | 98.4 | A | 45 |
| 12 | Acryloyloxymethyl-(dimethyl)methoxysilane[h] | 500 ppm of Ionox 220 | DH | 98.9 | N | 8 |
| 13 | Acryloyoxymethyl-(dimethyl)methoxysilane[h] | 500 ppm of Ionox 220 | TFV | 98.5 | N | 12 |
| C14[e] | Acryloyloxymethyl-(dimethyl)methoxysilane[h] | 1,000 ppm of BHT + 500 ppm of DPPA | DH | 98.9[i] | A | 28 |
| C15[e] | Acryloyloxymethyl-(dimethyl)methoxysilane[h] | 1,000 ppm of BHT + 500 ppm of DPPA | TFV | 98.1[g] | A | 33 |
| 16 | Methacryloyloxymethyl(dimethoxy)methylsilane[j] | 500 ppm of Ionox 220 | DH | 98.7 | N | 5 |
| 17 | Methacryloyloxymethyl(dimethoxy)methylsilane[j] | 500 ppm of Ionox 220 | TFV | 98.3 | N | 14 |
| C18[e] | Methacryloyloxymethyl(diethoxy)silane[j] | 1,000 ppm of Ethanox 703 | DH | 99.3[k] | A | 35 |
| C19[e] | Methacryloyloxymethyl(dimethoxy)methylsilane[l] | 1,000 ppm of Ethanox 703 | TFV | 98.7[g] | A | 38 |
| 20 | Methacryloyloxymethyl(diethoxy)methylsilane[l] | 500 ppm of Ionox 220 | TFV | 98.1 | N | 12 |
| C21[e] | Methacryloyloxymethyl(diethoxy)methylsilane[l] | 1,000 ppm of BHT + 500 ppm of DPPA | TFV | 98.1[g] | A | 26 |
| C22[e] | Methacryloyloxymethyl(diethoxy)methylsilane[l] | 1,000 ppm of Ethanox 703 | TFV | 98.2[g] | A | 36 |

[a]Ionox 220: 4,4'-Methylenebis(2,6-di-tert-butylphenol), BHT: 2,6-di-tert-butyl-4-methylphenol, DPPA: N,N'-diphenyl-p-phenylenediamine, Ethanox 703: 2,6-di-tert-butyl-4-(N,N-dimethylaminomethyl)phenol
[b]DH: Distillation head; TFV: thin-film evaporator
[c]N: neutral odor; A: odor of amine
[d]Obtained from potassium methacrylate and chloromethyltrimethoxysilane
[e]Example not according to the invention
[f]The bottom product of the distillation gelled after 20% of distillate had been obtained.
[g]Stopped after formation of polymer in thin-film evaporator.
[h]Prepared from triethylammonium acrylate and chloromethyl(dimethyl)methoxysilane
[i]The bottom product of the distillation gelled after 40% of distillate had been obtained.
[j]Prepared from potassium methacrylate and chloromethyl(dimethoxy)methylsilane
[k]The bottom product of the distillation gelled after 70% of distillate had been obtained.
[l]Prepared from potassium methacrylate and chloromethyl(diethoxy)methylsilane Stabilization efficiency:

In order to investigate the efficiency of the compounds of the formula I for stabilizing organosilicon compounds of the formula II which carry unsaturated groups, different stabilizers or stabilizer combinations were added, both under air and under argon, to unstabilized crude batches from syntheses of different unsaturated organosilicon compounds and tests were carried out to determine the time after which the crude mixtures gel at 140 or 150° C. with polymerization. The results are summarized in tables 2 and 3 below:

TABLE 2

Stabilization of crude 3-methacryloyloxypropyltrimethoxysilane (as in Example 1, but prepared without stabilizer), under argon.

| No. | Stabilizer | Result (gels after) |
|---|---|---|
| 23[a] | 0.025% of 4,4-methylenebis(2,6-di-tert-butylphenol) | 32 h at 150° C. |
| C24[b] | 0.05% of 2,6-di-tertbutyl-4-N-dimethyl-aminomethylenephenol | 10 h at 150° C. |
| C25[b] | 0.05% of 2,6-di-tert-butyl-4-methylphenol | 4 h at 150° C. |
| C26[b] | 0.05% of 2,6-di-tert-butyl-4-N-dimethyl-amino-methylenephenol + 0.05% of N,N'-diphenyl-p-phenylenediamine | 18 h at 150° C. |
| C27[b] | 0.05% of 2,6-di-tert-butyl-4-methylphenol + 0.05% of N,N'-diphenyl-p-phenylenediamine | 12 h at 150° C. |

[a] According to the invention
[b] Not according to the invention

Table 2 clearly shows that the compounds of the formula I result in substantial improvement in the thermal stability of a crude solution of 3-methacryloyloxypropyltrimethoxysilane, compared with the known compounds 2,6 di-tert-butyl-4-N-dimethylaminomethylenephenol and 2,6-di-tert-butyl-4-methylphenol, even if the latter are used together with a further inhibitor.

Experiments 23–27 were repeated at 140° C. under an air atmosphere. The results are summarized in table 3.

TABLE 3

Stabilization of crude 3-methacryloyloxypropyltrimethoxysilane in air.

| No. | Stabilizer | Result (gels after) |
|---|---|---|
| 28[a] | 0.025% of 4,4-methylenebis(2,6-di-tert-butylphenol) | 72 h at 140° C. |
| C29[b] | 0.05% of 2,6-di-tert-butyl-4-N-dimethylamino-methylenephenol | 45 h at 140° C. |
| C30[b] | 0.05% of 2,6-di-tert-butyl-4-methylphenol | 30 h at 140° C. |
| C31[b] | 0.05% of 2,6-di-tert-butyl-4-N-dimethylamino-methylenephenol + 0.05% of N,N'-diphenyl-p-phenylenediamine | 65 h at 140° C. |
| C32[b] | 0.05% of 2,6-di-tert-butyl-4-methylphenol + 0.05% of N,N'-diphenyl-p-phenylenediamine | 42 h at 150° C. |

[a] According to the invention
[b] Not according to the invention

Once again, it is found that the compounds of the general formula I result in superior stabilization.

The invention has further advantages as well. For example, the amount of compound of the formula I required for stabilizing unsaturated silicon-containing compounds is smaller than is the case with known compounds; the stabilizing effect lasts longer; the quality of the products with regard to color and odor with the use of the compounds of the formula I is substantially improved.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A process for stabilizing organosilicon compounds bearing unsaturated groups of the formula II:

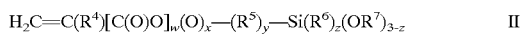

$$H_2C=C(R^4)[C(O)O]_w(O)_x-(R^5)_y-Si(R^6)_z(OR^7)_{3-z} \qquad II$$

during one or more of their preparation, distillation, or storage; wherein $R^4$ is a hydrogen atom or a linear or branched hydrocarbon radical having 1–10 carbon atoms; $R^5$ is a linear, cyclic or branched hydrocarbon radical having 1–40 carbon atoms optionally containing one or more heteroatoms selected from the group consisting of nitrogen, oxygen, sulfur and phosphorus; $R^6$ and $R^7$ are independently linear, cyclic, or branched hydrocarbon radicals having 1–10 carbon atoms, wherein w is 0 or 1, x is 0 or 1, y is 0 or 1, and z is 0, 1 or 2, and wherein w and x are not both 1 simultaneously, the compounds of the formula II having been obtained by reacting a haloalkylsilane with a salt of an unsaturated organic acid, by adding an effective stabilizing amount of one or more compounds of the formula I:

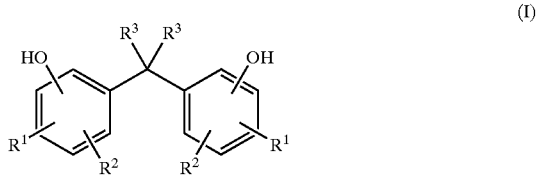

wherein $R^1$ and $R^2$ are identical or different linear or branched alkyl radicals having 1–20 carbon atoms and the radicals $R^3$ are identical or different substituents selected from the groups consisting of hydrogen and linear and branched alkyl radicals having 1–20 carbon atoms.

2. The process of claim 1, wherein the compound of the formula I is 4,4'-methylenebis(2,6-di-tert-butylphenol).

3. The process of claim 1, wherein the organosilicone compounds bearing the unsaturated groups comprise at least one compound of the formula II selected from the group consisting of 3-methacryloyloxypropyltrimethoxysilane, 3-methacryloyloxypropyl(dimethoxy)methylsilane, methacryloyloxymethyltrimethoxysilane, methacryloyloxymethyltriethoxysilane, methacryloyloxymethyl(dimethoxy)methylsilane, methacryloyloxymethyl(diethoxy)methylsilane, methacryloyloxymethyl(dimethyl)methoxysilane, methacryloyloxymethyl(dimethyl)ethoxysilane, 3-acryloyloxypropyltrimethoxysilane, 3-acryloyloxypropyl(dimethoxy)methylsilane, acryloyloxymethyltrimethoxysilane, acryloyloxymethyltriethoxysilane, acryloyloxymethyl(dimethoxy)methylsilane, acryloyloxymethyl(diethoxy)methylsilane, acryloyloxymethyl(dimethyl)methoxysilane, and acryloyloxymethyl(dimethyl)ethoxysilane.

4. The process as claimed in claim 1, wherein the amount of the stabilizing compound of the formula I used is from 0.001 to 1 percent by weight based on the weight of the organosilicon compound of the formula II.

5. The process as claimed in claim 1, wherein the amount of the stabilizing compound of the formula I used is from 0.005 to 0.5 percent by weight based on the weight of the organosilicon compound of the formula II.

6. The process of claim 1, wherein said compound of formula I is employed during reaction of said haloalkylsilane with said salt of unsaturated organic acid.

7. The process of claim 1, wherein said compound of formula I is added to said organosilicon compound of formula II prior to or during distallation of a composition containing the organosilicon compound of formula II.

8. The process of claim 1, wherein said compound of formula I is added to said organosilicon compound of the formula 11 prior to or during the storage of said organosilicon compound of formula II.

* * * * *

UNITED STATES PATENT AND TRADEMARK OFFICE
CERTIFICATE OF CORRECTION

PATENT NO.   : 6,841,694 B2
DATED        : January 11, 2005
INVENTOR(S)  : Juergen Pfeiffer It is certified that error appears in the above-identified patent and that said Letters Patent is hereby corrected as shown below:

Column 12,
Line 3, delete "11" and insert -- II --.

Signed and Sealed this

Twenty-sixth Day of April, 2005

JON W. DUDAS
*Director of the United States Patent and Trademark Office*